United States Patent [19]

Jung et al.

[11] Patent Number: 5,436,360
[45] Date of Patent: Jul. 25, 1995

[54] ALLYLALKYLPOLYSILOXANE TYPE SILICONE FLUIDS AND METHODS OF MAKING THEM

[75] Inventors: Il N. Jung; Bok R. Yoo; Bong W. Lee; Seung H. Yeon, all of Seoul, Rep. of Korea

[73] Assignee: Korea Institute of Science and Technology, Seoul, Rep. of Korea

[21] Appl. No.: 302,266

[22] Filed: Sep. 8, 1994

[30] Foreign Application Priority Data

Dec. 7, 1993 [KR] Rep. of Korea .............. 26737/1993

[51] Int. Cl.⁶ .......................... C07F 7/08; C07F 7/10; C07F 7/18
[52] U.S. Cl. .................................. 556/460; 556/415; 556/454; 556/456; 556/459; 556/461
[58] Field of Search ............... 556/415, 454, 456, 459, 556/460, 461

[56] References Cited

U.S. PATENT DOCUMENTS

| | | |
|---|---|---|
| 4,873,011 | 10/1989 | Jung et al. . |
| 4,965,385 | 10/1990 | Jung et al. . |
| 5,045,261 | 9/1991 | Suzuki .............. 556/460 X |
| 5,075,477 | 12/1991 | Jung et al. . |
| 5,233,069 | 8/1993 | Jung et al. . |
| 5,235,061 | 8/1993 | Jung et al. . |
| 5,235,083 | 8/1993 | Jung et al. . |
| 5,282,998 | 2/1994 | Horn et al. ......... 556/460 X |
| 5,302,734 | 4/1994 | Jung et al. . |
| 5,331,077 | 7/1994 | Braun et al. ........ 556/456 X |
| 5,332,849 | 7/1994 | Jung et al. . |
| 5,338,876 | 8/1994 | Jung et al. . |

*Primary Examiner*—Paul F. Shaver
*Attorney, Agent, or Firm*—Oblon, Spivak, McClelland, Maier & Neustadt

[57] ABSTRACT

The present invention relates to novel cyclic or linear allylpolysiloxane type silicone fluids having allylalkylsiloxy and diorganosiloxy groups as represented by the formula I and their preparation methods by hydrolyzing mixtures of allyldichlorosilane and diorganodichlorosilane as represented by the formula II and formula III respectively.

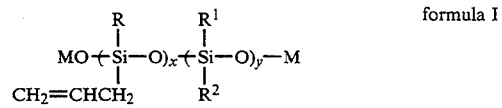

formula I

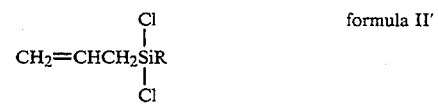

formula II'

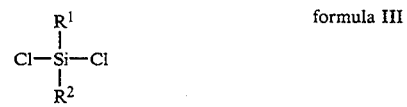

formula III wherein R is selected from the group consisting of hydrogen alkyl($C_3$-$C_{20}$), chloroalkyl, cyanoalkyl, fluoroalkyl, and phenylalkyl group; $R^x$ and $R^2$ represent independentlhydrogen, methyl or phenyl group; M represents H or $SiMe_3$ group wherein Me is methyl group and when M is hydrogen, the silanol groups at the both ends of the molecule easily undergo dehydration and cyclize to form the cyclic silicone fluids as represented by the following formula I'; the mixing ratio (x/y) of the compounds as represented in formula I and formula HI respectively can be 1:0.01–1:100; $CH_2CH_2R^3$ of formula II equals to R of formula I or I'.

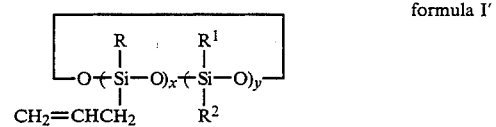

formula I'

12 Claims, No Drawings

ALLYLALKYLPOLYSILOXANE TYPE SILICONE FLUIDS AND METHODS OF MAKING THEM

BACKGROUND OF THE INVENTION

1. Field of the Invention

The present invention relates to novel cyclic or linear allylpolysiloxane type silicone fluids having allylalkylsiloxy and diorganosiloxy groups as represented by the formula I and their preparation methods by hydrolyzing mixtures of allyldichlorosilane and diorganodichlorosilane as represented by the formula II and formula III respectively.

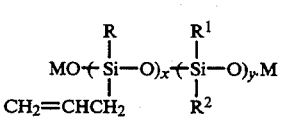

formula I

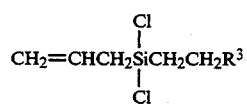

formula II

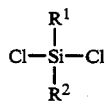

formula III wherein R is selected from the group consisting of hydrogen, alkyl($C_3$-$C_{20}$), chloroalkyl, cyanoalkyl, fluoroalkyl, and phenylalkyl group; $R^1$ and $R^2$ represent independentlhydrogen, methyl or phenyl group; M represents H or $SiMe_3$ group wherein Me is methyl group and when M is hydrogen, the silanol groups at the both ends of the molecule easily undergo dehydration and cyclize to form the cyclic silicone fluids as represented by the following formula I'; the mixing ratio (x/y) of the compounds as represented in formula II and formula III respectively can be 1:0.01–1:100; $CH_2CH_2{}^R{}_3$ of formula II equals to R of formula I or I'.

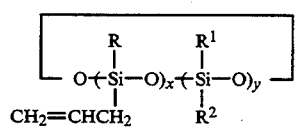

formula I'

2. Description of the Prior Art

In general, the preparation of organosilicone fluids is performed by the hydrolysis and condensation of organosilanes such as those having two methyl or other organic radicals bonded to the silicon atome. The hydrolysis is conducted by reacting a chlorosilane, such as dimethyldichlorosilane, with water, generally in the presence of an inert solvent. The organosilicone fluids are thus obtained without difficulty. (Wilcock, U.S. Pat. No. 2,491,843, Patnode and Wilcock, *J. Am. Chem. Soc.*, 68, 358(1946)) Dimethyldichlorosilane gives with water a mixture of cyclic polydimethylsiloxanes and linear polydimethylsiloxane-α,ω-diols. Depending upon the hydrolysis methods, the ratio of cyclic and linear fluids in the products varies. Polydimethylsiloxanes are the most common silicone fluids and the special type silicone fluids having other organic groups than methyl at silicon atom are also commercially available. When allylalkydichlorosilane is hydrolyzed, polyallylalkylsiloxanes type fluid is obtained. Since they are hydrosilated with polymethylhydridosiloxanes and a rubbery material is obtained, they am used for the manufacture of two-components room temperature vulcanizing rubber. (T. Fukuda and S. Yumoto, U.S. Pat. No. 4,528,516)

The chlorosilanes may be dissolved in an inert organic solvent such as toluene, benzene, carbon tetrachloride, ether, liquid aliphatic hydrocarbons before hydrolysis. The fluids obtained directly from the hydrolysis of diogranodichlorosilanes are of course seldom the final products in a technical sense. The molecular weights of these fluids are not very high and they have tendency to undergo further condensation due to the silanol groups at the ends of the molecule. Low-molecular-weight polydiorganosiloxanes, particularly cyclic ones, can be convened into high-molecular-weight products. This polymerization reaction is normally catalyzed by strong acids or bases. The molecular weight of the polymer, and consequently its viscosity, is controlled through end-blocking by triorganosilane. For the standard dimethyl silicone fluids, this end-blocking agent is usually hexamethyldisiloxane. D. F. Wilcock disclosed in U.S. Pat. No. 2,491,843 that cyclic methylhydridopolysiloxane could be equilibrated with hexamethyldisiloxane in the presence of concentrated sulfuric acid to give trimethylsilyl group end-blocked straight-chain polydimethylsiloxane fluid of randomly distributed molecular weight.

The present inventors reported that allyldichlorosilane as the major product and allyltrichiorosilane were prepared by reacting allyl chloride, incorporated with hydrogen chloride, with elemental silicon in the presence of copper catalyst at a temperature from 260° C. to 360° C. Cadmium was a good promoter and the reaction could be carded out in a fluidized bed or a stirred bed reactor. The incorporation of hydrogen chloride suppressed the decomposition of allyl chloride and prevented the production of diallyldichlosilane. Diallyldichlosilane easily caused the polymerization of the products at the reaction temperature. [Korean Patent Application No. 92-10292 (92.6.13)]

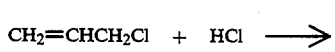

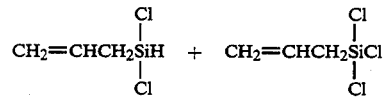

The present inventors also reported that allyldichlorosilane could be hydrosilated with unsaturated organic compounds to give allylalkyldichlorosilanes in the presence of chloroplatinic acid catalyst at the reaction temperature from 50° C. to 80° C. [Korean Patent Application No. 93-26069 (93.12.1)]

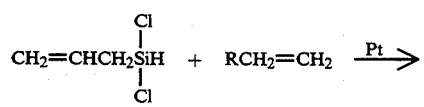

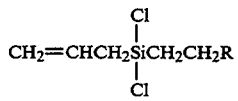

SUMMARY OF THE INVENTION

The present invention relates to novel cyclic or linear allylpolysiloxane type silicone fluids having allylalkylsiloxy and diorganosiloxy groups as represented by the formula I and their preparation methods by hydrolyzing mixtures of allyldichlorosilane and diorganodichlorosilane as represented by the formula 1I and formula 1II respectively.

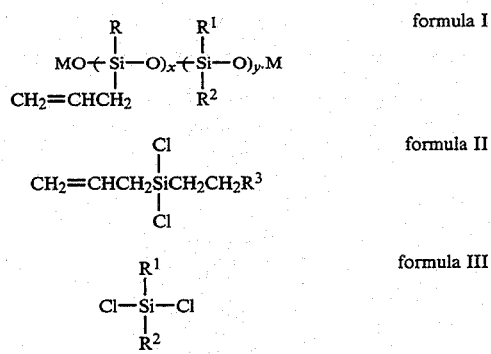

wherein R is selected from the group consisting of hydrogen alkyl($C_3$–$C_{20}$), chloroalkyl, cyanoalkyl, fluoroalkyl, and phenylalkyl group; $R^1$ and $R^2$ represent independentlhydrogen, methyl or phenyl group; M represents H or $SiMe_3$ group wherein Me is methyl group and when M is hydrogen, the silanol groups at the both ends of the molecule easily undergo dehydration and cyclize to form the cyclic silicone fluids as represented by the following formula I'; the mixing ratio (x/y) of the compounds as represented in formula II and formula III respectively can be 1:0.01–1:100; $CH_2CH_2R^3$ of formula II equals to R of formula I or I'.

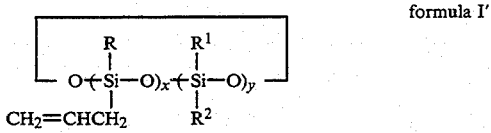

Allylpolysiloxane type silicone fluids as represented by the formula I having diorganosiloxy and allylhydridosiloxy groups may be prepared by any suitable methods. For example, allylhydridopolysiloxanes end-blocked with the hydroxy group or trimethylsiloxy groups are prepared by hydrolyzing allyldichlorosilane or a mixture of trimethylchlorosilane and allyldichlorosilane. The chlorosilanes may be dissolved in an inert organic solvent such as toluene, benzene, carbon tetrachloride, ether, liquid aliphatic hydrocarbons, etc. and then hydrolyzed by pouring the solution into water or the other way around. After hydrolysis the solution has been thoroughly washed with water to remove all, or substantially all, of the hydrochloric acid and then the solvent may be distilled to give the fluids. Allylhydridopolysiloxanes end-blocked with hydroxy group are prepared by hydrolyzing allyldichlorosilane only. The same fluids end-blocked with trimethylsiloxy groups may be prepared by co-hydrolyzing allyldichlorosilane and trimethylchlorosilane or equilibrating allylhydridopolysiloxanes end-blocked with hydroxy group and hexamethyldisiloxane using concentrated sulfuric acid or $CF_3SO_3H$. The copolymers containing allylorganosiloxy- and dialylsiloxy- groups may be prepared by co-hydrolyzing allylalkyldichlorosilane and diorganodichlorosilane and then equilibrating the products with hexamethyldisiloxane. The same fluids may be prepared by equilibrating allylhydridopolysiloxanes end-blocked with trimethylsiloxy group and cyclic diorganopolysiloxanes using concentrated sulfuric acid or $CF_3SO_3H$. The concentration of the catalyst used can be 400–4,000 ppm respect to the polysiloxane.

The cleavage of allyl group attached to silicon have been reported to give off propylene and the cleavage reaction is accelerated by strong acids or bases. (D. L. Balley and A. N. Pines, Industrial and Engineering Chemistry, 1954, 46, 2363) Allylchlorosilanes do not undergo cleavage of the carbon-silicon bond when the hydrolysis is carried out in the presence of excess pyridine or sodium bicarbonate. Therefore in the hydrolysis of allylchlorosilanes, particularly allyldichlorosilane, the use of a hydrogen chloride acceptor is an important feature of the reaction and lower reaction temperatures are preferable in hydrolysis. Thus, the use of an inert solvent is suggested to prevent rising the reaction temperature due to the heat of hydrogen chloride hydration. In the following examples, the products from the reactions have been identified by spectroscopic methods such as gas chromatography and nuclear magnetic resonance(nmr) spectroscopy. Abbreviations for nmr spectra are s=singlet, d=doublet, t=triplet, q=quartet, m=multiplet; peak positions are reported as parts per million on the basis of the internal tetramethylsilane. The molecular weights of the products have been determined by Gel Permeation Chromatography (GPC).

The present invention will be further illustrated by the following examples. It is, however, not intended to restrict the present invention to these examples.

EXAMPLE 1

Preparation of allylhydridocyclopolysiloxanes

To a 100 ml, three neck, round bottomed flask equipped with a mechanical stirrer, a dropping funnel, and a reflux condenser were added 10 g (0.071 mole) of allyldichlorosilane and 20 ml of diethyl ether. 100 ml of water was added dropwise through the dropping funnel with stirring and agitation was continued for another hour to complete the hydrolysis. The organic layer was separated from the aqueous layer, neutralized with sodium carbonate solution, and dried over anhydrous magnesium sulfate. The solution was filtered and the organic solvent was evaporated to give 5.26 g (95.1%) of the oily products.

The product compositions and their $^1$H-NMR data are following;

1,3,5,7-tatraallylcyclotetrasiloxane, 2.10 g(41.2% ): $^1$H-NMR ($\delta CDCl_3$) 5.68–5.83 (m, 1H, CH), 4.97–5.03(m, 2H, $CH_2$=), 4.63–4.64(br. t, 1H, Si-H), 1.65–1.70(d, 2H, -$CH_2$-).

1,3,5,7,9-pentaallylcyclopentasiloxane, 1.56 g(29.6%): $^1$H-NMR ($\delta CDCl_3$) 5.71–5.80 (m, 1H,-CH-), 4.96–5.01(m, 2H, $CH_2$=), 4.63–4.65(br. t, 1H, Si-H), 1.65–1.68(d, 2H, -$CH_2$-).

1,3,5,7,9,11-hexaallylcyclohexasiloxane and 1,3,5,7,9,11,13-heptaallylcycloheptasiloxane were obtained with 11.1% and 3.2% yields, respectively. The linear α,ω-dihydroxypolysiloxane material (MW:700–40,000) was also obtained in small quantity. $^1$H-NMR data of the linear material were similar to those of cyclopolysiloxane.

EXAMPLE 2

Preparation of allylhydridodimethylpolysiloxanes

By the same conditions and procedure in Example 1, a mixture of 5 g (0.035 mole) allyldichlorosilane, 4.57 g(0.035 mole) dimethyldichlorosilane, and 30 ml of diethyl ether were hydrolyzed. 8.46 g (74.9%) oily products was obtained.

The product compositions and their $^1$H-NMR data are following;

The 1:1 isomeric mixture of 1,3-diallyl-5,5,7,7-tatramethylcyclotetrasiloxane and 1,5-diallyl-3,3,7,7-tetramethylcyclotatrasiloxane, 2.23 g (27.2%); $^1$H-NMR ($\delta$ CDCl$_3$) 5.69–5.82(m, 1H, CH), 4.89–5.08(m, 2H, CH$_2$=), 4.57–4.62 (t, 1H, Si-H), 1.07–1.19 (d, 2H,-CH$_2$-), 0.14 (s, 12H, CH$_3$).

1-Allyl-3,3,5,5,7,7-hexamethylcyclotatrasiloxane, 1.34 g (15.8%); $^1$H-NMR($\delta$ CDCl$_3$) 5.68–5.83(m, 1H, CH), 4.93–4.99(m, 2H; CH$_2$=), 4.54–4.67(t, 1H, Si-H), 1.56–1.62(d, 2H, -CH$_3$), 0.16(S, 12H, CH$_3$).

The polymeric material (MW: 700–2,000) was also obtained in small quantity. $^1$HNMR data of the polymeric material were similar to those of cyclopolysiloxane. Besides the products mentioned above hexamethyldisiloxane and octamethyltetrasiloxane were obtained with 7.7% and 7.9% yields, respectively.

EXAMPLE 3

Preparation of α,ω-di(trimethylsilyl)allylhydridopolysiloxanes

There was mixed in a reaction flask 2.3 g (0.029 mole) of allylhydridocyclosiloxane and 0.94 g (0.006 mole) of hexamethyldisiloxane. To this mixture there was added 0.023 g of H$_2$SO$_4$. This resulting mixture was stirred for one hour at room temperature and heated at a temperature of 60° C. for 2 hours.

The H$_2$SO$_4$ was withdrawn from the bottom of the flask and 20 ml of n-Hexane was added to the oily mixture. The organic layer was washed with water three times and dried over anhydrous magnesium sulfate. The solution was filtered and the organic solvent was evaporated to give 1.02 g of oily products.

The product compositions and their $^1$H-NMR data are following;

3-Allyl- 1,1,1,5,5,5-hexamethyltrisiloxane, 0.46 g (45.3%); $^1$H-NMR(6 CDCl$_3$) 5.67–5.79(m, 1H, CH), 4.90–4.96(m, 2H, CH$_2$=), 4.514.56(t, 1H, Si-H), 1.56–1.57(d, 2H, -CH$_2$-), 0.09(s, 18H, CH$_3$).

3,5-Diallyl-1,1,1,7,7,7-hexamethyltetrasiloxane, 0.05 g (9.9%); $^1$H-NMR ($\delta$ CDCl$_3$) 5.02–5.45(m, 1H, CH), 4.90–4.78(m, 2H, CH$_2$=), 4.62–4.71(t, 1H, Si-H), 1.48 –1.52(d, 2H,-CH$_2$), 0.08(s, 18H, CH$_3$).

3,5,7-Triallyl- 1,1,1-9,9,9-hexamethylpentasiloxane and 3,5,7,9-tetraallyl- 1,1,1,11,11,11-hexamethyltetrasiloxane were obtained with 10.9% and 3.7% yields, respectively.

The polymeric material (MW:800–40,000) was also obtained in small quantity. $^1$H-NMR data of the polymeric material were similar to those of cyclopolysiloxanes.

EXAMPLE 4

Preparation of α,ω-di(trimethylsilyl)allylhydridodimethylpolysiloxanes

By the same conditions and procedure in Example 3, a mixture comprising 10 g (0.03 mole) of octamethylcyclotetrasiloxane, 0.66 g (0.03 mole) of allylhydridocyclopolysiloxane, and 1.38 g (0.008 mole) of hexamethyldisiloxane was equilibrated using 0.006 g of H$_2$SO$_4$.

H$_2$SO$_4$ was withdrawn from the bottom of the flask and 20 ml of n-Hexane was added to the oily mixture. The organic layer was washed with water three times and dried over anhydrous magnesium sulfate. The solution was filtered and the organic solvent was evaporated to give 2.83 g of oily products.

The product compositions and their $^1$H-NMR: 5.69–5.83(m, 1 H, CH$_3$), 4.93–4.99(m, 2H, CH$_2$), 4.57–4.58(t, 1H, Si-H), 1.53–1.63(d, 2H, CH$_2$), 0.13(S, 18H, CH$_3$).

1-Allyl-3,3,5,5,7,7,9,9-octamethylcyclopentasiloxane, 0.20 (7.1%), octamethyltetrasiloxane, 0.42 g(14.8%), dimethylcyclopolysiloxanes (40%), 1-allyl-3,3,5,5,7,7hexamethylcyclotetrasiloxane, 0.45 g(15.9%), and 1-allyl-3,3,5,5,7,7,9,9-octamethylcyclopentasiloxane, 0.20 g (7.1% ) were obtained.

The polymeric material (MW:800–40,000) was also obtained in small quantity. $^1$H-NMR data of the polymeric material were similar to those of cyclopolysiloxanes.

EXAMPLE 5

Preparation of allylhydridomethylphenylcyclopolysiloxanes

By the same conditions and procedure in Example 1, a mixture of 5 g (0.035 mole) allyldichlorosilane, 6.7 g (0.035 mole) dichloromethylphenylsilane, and 30 ml of diethyl ether were hydrolyzed. 8.5 g of oily products was obtained.

The product compositions and their $^1$H-NMR data are following;

The product mixture comprising 2.91 g (35%) of diallyldimethyldiphenylcyclotetrasiloxane two isomeric mixture, 2.3 g (27%) of 1-allyl-3,5,7-trimethyl-3,5,7-triphenylcyclotetrasiloxane, and 1.1 g (13%) of triallyldimethyldiphenylpentasiloxane (two isomeric mixture) were obtained.

Diallyldimethyldiphenylcyclotetrasiloxane (two isomeric mixture), $^1$H-NMR: 7.21–7.67(s, 10H, Phenyl-H), 5.70–5.83(m, 2H, CH), 4.80–5.03(m, 4H, CH$_2$), 4.60–476. (t, 2H, Si-H), 1.50–1.78(br.d, 4H, CH$_2$), 0.33–0.58(br.s, 6H, CH$_3$).

The polymeric material (MW: 800.40,000) was also obtained in small quantity. $^1$H-NMR data of the polymeric material were similar to those of cyclopolysiloxane.

EXAMPLE 6

Preparation of allylalkyldimethylsiloxanes

The same procedure as Example 5 was repeated except that a mixture of allyl(3-chloropropyl)dichlorosilane 7.6 g (0.035 mole), dimethyldichlorosilane 4.57 g (0.035 mole), and diethyl ether 30 ml (0.28 mole) was hydrolyzed. The same procedure was repeated except using various allylalkyldichlorosilanes instead of allyl(3-chloropropyl) dichlorosilane.

The oily products were devolatilized under vacuum to remove cyclic dimethylsiloxanes and 92–95 % of the oily products remained. About 40–60% of the final products contained 1,3-diallyl-1,3-dialkyl-1,3-dihydroxydisiloxanes and their oligomers containing dimethylsiloxane group. The remainder contained polymeric materials (MW: 700–40,000).

$^1$H-NMR data of various 1-allyl-1-alkyl-3,3,5,5,7,7-hexamethyltetrasiloxanes are listed in Table 1. $^1$H-NMR data of the polymeric material were similar to those of cyclopolysiloxanes.

TABLE 1

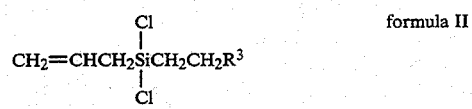

| R | CH$_3$(s) | SiCH$_2$ | CH$_2$ | SiCH$_2$(d) | =CH$_2$ | =CH | R |
|---|---|---|---|---|---|---|---|
| CH$_2$Cl | 0.12 | 0.49–0.62 | 1.65–1.78 | 1.57 | 5.08–5.16 | 5.69–5.80 | 3.33(t, 2H, CH$_2$) |
| CN | 0.12 | 0.58–0.65 | 1.63–1.77 | 1.56 | 5.07–5.15 | 5.68–5.82 | — |
| CH$_2$CN | 0.13 | 0.56–0.67 | 1.59–1.78 | 1.49 | 5.07–5.14 | 5.67–5.82 | 2.41(t, 2H, CH$_2$) |
| CF$_3$ | 0.13 | 0.51–0.63 | 1.59–1.77 | 1.39 | 5.07–5.15 | 5.69–5.85 | — |
| CH$_2$CF$_3$ | 0.12 | 0.52–0.64 | 1.55–1.75 | 1.39 | 5.06–5.14 | 5.70–5.85 | 2.01–2.35(m, 2H, CH$_2$) |
| CH$_3$ | 0.10 | 0.59–0.61 | 1.42–1.59 | 1.29 | 5.06–5.14 | 5.71–5.87 | 0.90(t, 3H, CH$_3$) |
| (CH$_2$)$_2$CH$_3$ | 0.10 | 0.48–0.62 | 1.23–1.56 | 1.29 | 5.06–5.15 | 5.72–5.86 | 0.90(t, 3H, CH$_3$), 1.23–1.56(m, 6H, CH$_2$) |
| (CH$_2$)$_{15}$CH$_3$ | 0.10 | 0.48–0.62 | 1.23–1.56 | 1.28 | 5.05–5.14 | 5.71–5.87 | 0.90(t, 3H, CH$_3$), 1.23–1.56(m, 6H, CH$_2$) |
| Ph | 0.13 | 051–0.63 | 1.54–1.69 | 1.46 | 5.05–5.15 | 5.69–5.83 | 7.18–7.32(m, 5H, Phenyl-H) |

EXAMPLE 7

Preparation of allylalkylhydridomethylsiloxane

The same procedure as Example 6 was repeated except that hydridomethyldichlorosilane 4.0 g (0.035 mole), was used instead of dimethyldichlorosilane.

The oily products were devolatilized under vacuum to remove cyclic dimethylsiloxanes and 90–96 % of the oily products remained. About 40–54 % of the final products consisted of 1,3-diallyl-1,3-dialkyl-1,3-dihydroxydisiloxanes and their oligomers containing hydridomethylsiloxane group. The remainder contained polymeric materials (MW:. 700–40,00).

$^1$H-NMR data of various polymeric materials containing allylalkylsiloxane and hydridomethylsiloxane groups were similar to those of polysiloxane listed in Table 1 except Si-H peaks (4.60–4.75 ppm).

What is claimed is

1. Cyclic or linear allylpolysiloxane silicone fluids having allylorganosiloxy and diorganosiloxy groups as represented by the formula I and I'

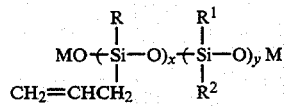

where, R is selected from the group consisting of hydrogen, alkyl(C$_3$–C$_{20}$), chloroalkyl, cyanoalkyl, fluoroalkyl, and phenylalkyl group; R$^1$ and R$^2$ represent independently hydrogen, methyl or phenyl group; M represents H or SiMe$_3$ group wherein Me is methyl group and when M is hydrogen, the silanol groups at the both ends of the molecule easily undergo dehydration and can cyclize to form the cyclic silicone fluids as represented by the formula I'

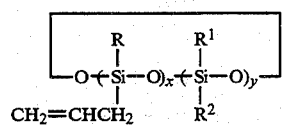

wherein R, R$^1$ and R$^2$ are as above defined; and the ratio (x/y) can be 1:0.01–1:100.

2. A method for preparing the allylpolysiloxane type silicone fluids having allylorganosiloxy and diorganosiloxy groups as represented by the formula I and I' of claim 1 wherein M is hydrogen, by hydrolyzing a mixture of allyldichlorosilane as represented by the formula II and diorganodichlorosilanes as represented by the formula III in the presence or absence of organic solvent

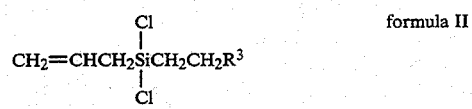

wherein the mixing ratio of the compounds as represented by the formula II and formula III respectively can be 1:0 01–1:100, in the formula III CH$_2$CH$_2$R$^3$ is same as R in the formulas I and I' of claim 1.

3. A method for producing the allylpolysiloxane type linear silicone fluids as represented by the formula I of claim 1, wherein M is trimethylsiloxy group, by hydrolyzing the mixture of allyldichlorosilane as represented by the formula II, diorganodichlorosilane as represented by the formula III, and trimethylchlorosilane in the presence or absence of organic solvent.

4. A method for producing the allylpolysiloxane type linear silicone fluids as represented by the formula I of claim 1, wherein M is trimethylsiloxy group, by equilibrating the cyclic silicone oil as represented by the formula I' with hexamethyldisiloxane using concentrated sulfuric acid or CF$_3$SO$_3$H as a catalyst.

5. The allylpolysiloxane type silicone fluids according to claim 1, wherein R is phenylalkyl group.

6. The allylpolysiloxane type silicone fluids according to claim 1, wherein R is cyanoalkyl group.

7. The allylpolysiloxane type silicone fluids according to claim 1, wherein R is chloroalkyl group.

8. The allylpolysiloxane type silicone fluids according to claim 1, wherein R is fluoroakyl group.

9. The allylpolysiloxane type silicone fluids according to claim 1, wherein R is C$_1$–C$_{20}$ alkyl group.

10. The allylpolysiloxane type silicone fluids according to claim 1, wherein $R^1$ and $R^2$ are both methyl.

11. The allylpolysiloxane type silicone fluids according to claim 1, wherein $R^1$ and $R^2$ are hydrogen and methyl group respectively.

12. The allylpolysiloxane type silicone fluids according to claim 1, wherein $R^1$ and $R^2$ are methyl and phenyl group respectively.

* * * * *